United States Patent [19]

Lewis

[11] 4,255,663

[45] * Mar. 10, 1981

[54] DISPOSABLE LIQUID STERILIZER UNIT

[76] Inventor: James H. Lewis, P.O. Box 2341, London, Canada

[*] Notice: The portion of the term of this patent subsequent to Feb. 27, 1996, has been disclaimed.

[21] Appl. No.: 1,580

[22] Filed: Jan. 8, 1979

Related U.S. Application Data

[63] Continuation-in-part of Ser. No. 781,021, Mar. 24, 1977, Pat. No. 4,141,686.

[51] Int. Cl.³ .......................... A61L 2/10; A61L 2/26
[52] U.S. Cl. ................................... 250/436; 250/438; 313/27; 422/24
[58] Field of Search .................. 422/24, 186; 210/243; 250/428, 432 R, 436, 438, 455; 313/21, 26, 27

[56] References Cited

U.S. PATENT DOCUMENTS

| | | | |
|---|---|---|---|
| 1,091,221 | 3/1914 | Henri et al. | 313/27 |
| 1,307,500 | 6/1919 | Keyes | 313/27 |
| 4,141,686 | 2/1979 | Lewis | 422/24 |

FOREIGN PATENT DOCUMENTS

498015 12/1953 Canada .
1295774 5/1962 France ...................... 250/432

Primary Examiner—Bradley Garris
Attorney, Agent, or Firm—Townsend and Townsend

[57] ABSTRACT

A disposable liquid sterilizer unit incorporates an ultra-violet tube designed to generate radiation at approximately 2537 Angstroms. The unit comprises an elongated cylindrical plastic jacket opaque to ultra-violet radiation concentrically mounted about the tube to provide a chamber between the jacket and the tube for the flow of liquid to be exposed to radiation generated by the tube. The tube extends beyond the ends of the jacket and includes electrical connectors at each end for removably mounting the unit to make electrical connection with electrical connections in a casing. A seal is provided adjacent each end of the jacket against liquid flow from the chamber between the tube and the walls of the jacket to the exterior of the jacket. Inlet and outlet connections for the flow of water to and from the chamber are provided. The tube is double-walled, providing a sealed and preferably evacuated space between the walls to provide thermal insulation between the radiation generating parts (gas and electrodes) inside the inner wall and the outer surface of the outer wall which is exposed to cold water in the flow chamber.

5 Claims, 17 Drawing Figures

DISPOSABLE LIQUID STERILIZER UNIT

CROSS-REFERENCE TO OTHER APPLICATION

This application is a continuation-in-part of application Ser. No. 781,021 filed Mar. 24, 1977, now U.S. Pat. No. 4,141,686 issued Feb. 27, 1979.

BACKGROUND OF THE INVENTION

This invention relates to liquid sterilizers and more particularly to water sterilizers employing ultra-violet radiation to kill bacteria.

It is well known to sterilize water by exposing the water to ultra-violet radiation at a wavelength of approximately 2537 Angstroms. In a typical sterilizer, water is exposed to ultra-violet radiation as it is introduced through an inlet into a cylinder housing an ultra-violet tube, the water then flowing through the length of the cylinder where it exits through an outlet. The water is sterilized as it is exposed to the ultra-violet radiation generated by the tube.

It is also known to sterilize water by exposing the water to ozone generated at a wavelength of approximately 1880 Angstroms. The ozone can be generated by means of a tube of similar construction to that of an ultra-violet radiation generator, or by means of an electrical arc generated in the water. The known ozone generator leaves a residue of ozone in the water, which continues to sterilize the water as it passes through the cylinder.

It is also possible to sterilize water utilizing gamma ray radiation. Thus, the principles of this invention apply to all of these known kinds of sterilizers. However, the invention will be specifically described with reference to embodiments employing ultra-violet radiation.

Although sterilization of water by use of ultra-violet radiation has an excellent reputation for killing bacteria, such sterilizers have tended to be expensive, and also require specialized skills for installation and maintenance. However, there is a need for a water sterilizer that a home or cottage owner can afford and can install and maintain without having specialized skills.

One of the problems associated with known sterilizers, which contributes to their complexity, is that they are designed as permanent installations, except for the replacement of worn out or defective bulbs. As a consequence, these sterilizers have complex mounting arrangements for the tube, the end seal connections and the water inlet and outlet. Also, because the known sterilizers were designed as permanent installations, the water supply connections tended to be complex, again requiring specialized skills for installation. Since the tubes are also quite delicate, there is a serious risk of tubes being broken on replacement, if done by anyone other than a trained technician.

An example of a prior art sterilizer of complex design is described in Canadian Pat. No. 610,989, which issued to Corn Products Company on Dec. 20, 1960. This patented sterilizer was clearly designed as a permanent installation except for replacement of the ultra-violet tubes. For example, the inlet and outlet ports are formed of conduits, nipples, adapters, gaskets and screws. The ends of the ultra-violet tubes are connected to electrical sockets that are mounted on connector blocks slidably mounted on connector block plates and locked in place. When a tube is to be replaced, these connectors have to be removed from the connector blockplates. It can be readily appreciated that specialized skills are thus required both for initial installation and maintenance. Resealing of the sterilizer when replacing a lamp also poses a problem.

As is well known, ultra-violet tubes operate more efficiently at higher temperatures. One known type of water sterilizer, therefore, provides a protective quartz sheath surrounding the tube, thereby leaving an air space between the sheath and the tube to provide insulation for the tube from the water flowing around the sheath. However, such sheaths suffer from the disadvantage of having to be cleaned periodically to remove collected dust, which can inhibit the penetration of light from the tube through the sheath to the water, resulting in reduced efficiency and risk of non-sterilization. Thus, the cleaning of the sheaths has to be done by a skilled technician. Special handling is also required, especially because the quartz is susceptible to finger prints, and because the quality of quartz required produces a fragile sheath that can be broken very easily. From the above discussion, it can be appreciated that prior art water sterilizers employing sheaths are expensive and require specialized skills for their installation and maintenance. Canadian Pat. No. 610,989 employs such a quartz sheath, adding to the complexity, fragility and cost of the sterilizer.

Other known prior art sterilizers employ sensing devices to sense the amount of light radiated by the ultra-violet tube, coupled with an electro-magnetic control device to control valves at the water inlet. Thus, if the tube is not emitting sufficient light to sterilize, the valve at the inlet is closed and the unit fails safe. Although serving a useful purpose, such fail safe devices add to the expense of a sterilizer unit. A prior art sterilizer employing such a fail safe device is described in Canadian Pat. No. 674,555, which issued to Allsafe Water Sterilizer Ltd. on Nov. 19, 1963. The Allsafe sterilizer is another example of one employing a protective sheath and designed as a permanent installation except for replacement of lamps, again involving a complex mechanical end cap arrangement requiring specialized skills for maintenance.

Canadian Pat. No. 767,856 granted Sept. 26, 1967 and Canadian Pat. No. 841,135, granted May 5, 1970, and invented by James W. Harrison, are further examples of sterilizers that are designed to fail safe. The sterilizers described in these patents are of the permanent installation type requiring the removal of end caps for replacement of ultra-violed tubes.

I am also aware of the sterilizers disclosed in Canadian Pat. No. 357,083 issued Apr. 7, 1936 to James et al. and No. 739,145 issued July 26, 1966 to Filion.

My application Ser. No. 781,021 referred to above discloses a disposable unit that consists essentially of an elongated tube for generating the sterilizing radiation and a similarly shaped outer jacket opaque to the radiation. The tube extends coaxially along the jacket while forming a flow chamber between them, i.e. between an outer cylindrical surface of the tube and an inner cylindrical surface of the jacket. Water is caused to travel along this flow chamber from an inlet at one end of the jacket to an outlet at the other end. The quartz sheath that had traditionally been located around the tube in the majority of prior art constructions (see for example Canadian Pat. No. 610,989 referred to above) has been omitted from my prior construction, the water coming into direct contact with the tube surface. This omission of the intermediate quartz sheath represented a significant cost saving and was largely responsible for the ability to make the unit a disposable one. By reference to "disposable" it is intended to state that the tube is or can be non-removably mounted in the jacket by means of liquid tight seals at each end, so that when the tube is burnt out the whole unit is discarded.

In the specific form of unit disclosed in my said earlier application (patent), the ends of the tube project beyond the ends of the jacket in which they are mounted. These projecting tube ends providing terminals that serve both for establishing the necessary electrical connections and for mechanically supporting the unit in an outer protective casing.

In using a "disposable" unit, no attempt is made to remove a used tube from its jacket. Once a year or as found necessary, the whole unit is removed from the casing and discarded, and a new unit is fitted. This operation can be carried out by an unskilled person as easily as changing an electric light bulb. Such an operation contrasts with the practice prior to my earlier invention, which involved the services of a skilled technician to remove the old tube from the jacket and replace it with a new one, while handling the quartz sheath very carefully. Even so it was often found impossible to avoid breakage of the quartz sheaths.

My prior development was thus a significant step forward in the art, in that it reduced the cost of each unit (jacket and tube) and simplified the mounting thereof in a casing. This simplification was sufficient to render it economically preferable to treat each unit as a disposable one and thus avoid the need for the services of a skilled technician. As a result, my prior development has already enjoyed significant success in the market place.

However, the direct contact between the water and the tube that resulted from elimination of the quartz sheath has one disadvantage along with its many advantages. Apart from the cost advantage of a disposable unit that has already been discussed, another advantage was elimination of the condensation and dust build up that had previously been experienced in the air space between the tube and the sheath.

The disadvantage, on the other hand, arose from the fact that the direct contact between the often cold incoming water and the tube could sometimes lower the temperature of the tube below its operational optimum, thus reducing the amount of ultra-violet emission. In practice, this problem could lead to the use of a tube larger than that normally required, in order to have sufficient spare capacity to be able to compensate for the lowered efficiency of the tube under adverse temperature conditions.

The present invention is an improvement over my prior development described above, in that it avoids this disadvantage without going back to the problems of the earlier sheath-type of construction. In other words, the present invention retains the essential merits of my prior development, i.e. cheapness and ease of installation and hence disposability, while at the same time recapturing and improving upon an advantage afforded by the sheath type design, namely thermal insulation of the tube from cold incoming water.

This aim has been achieved in the present invention by making the tube a double-walled tube, i.e. a tube having inner and outer cylindrical walls sealed together and spaced apart from each other so as to define a sealed space between them. The outer surface of the outer wall is in contact with the liquid in the flow chamber defined between the tube and the jacket, while the conventional means for generating the radiation is located within the inner wall. As a result, the intermediate space, which may be evacuated, provides thermal insulation between such generating means and any cold liquid in the flow chamber.

For a fuller understanding of the nature and advantages of the invention, reference should be had to the ensuing detailed description taken in conjunction with the accompanying drawings.

DESCRIPTION OF EMBODIMENTS

FIGS. 1 to 4a show a disposable water sterilizer unit 20, which essentially comprises an elongated cylindrical plastic jacket 21, typically made of plastic tubing, and a double-walled, ultra-violet lamp or tube 22 designed to radiate light at a wavelength of approximately 2537 Angstroms to sterilize water or other liquid exposed to this ultra-violet radiation.

Figures 1, 2:
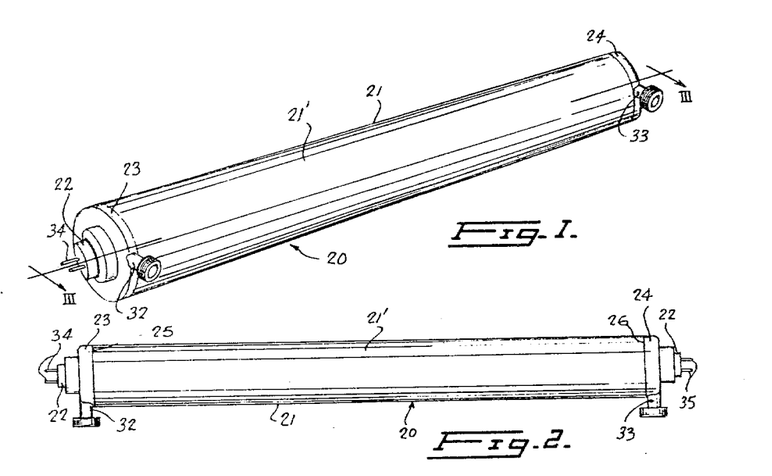
FIG. 1 is a perspective view of a disposable water sterilizer unit.
FIG. 2 is a plan view of the same unit.
Figure 3:
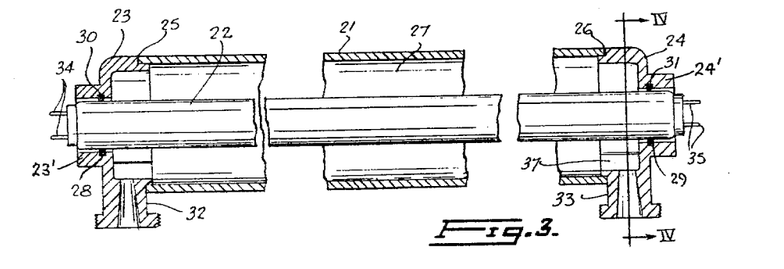
FIG. 3 is a horizontal sectional view of the unit taken along lines III—III of FIG. 1, showing the tube and the end sealing arrangements.

The jacket 21 is composed of a central portion 21' and end portions 23 and 24. These end portions are injection moulded parts and are fixed to the central portion 22 at 25 and 26 by means of a suitable adhesive. Of course, the jacket 21 can be formed of a single moulded part.

As can be seen from FIG. 3, the jacket 21 is concentrically mounted about the cylindrical tube 22 to provide a chamber 27 between the internal surface of the jacket and the external surface of the tube for the flow of water to be sterilized. The tube 22 passes through and beyond the end portions 23 and 24 of the jacket. The tube 22 is non-removably supported by the end portions 23 and 24 by means of a close fit between the tube and neoprene sealing rings 28 and 29 located in grooves 30 and 31 in reduced diameter extreme ends 23' and 24'. These rings 28, 29 also provide a seal against water flow from the chamber 27 to the exterior of the jacket 21.

Water inlet and outlet connections 32 and 33 are also moulded as part of the end portions 23 and 24 respectively, to provide connections to and from a water supply with access to the chamber 27. It can be seen that the connections 32 and 33 are threaded at their ends for easy connection to the plumbing system.

Prongs or terminals 34 and 35 at the ends of the tube 22 serve as electrical and mechanical connection means externally of the jacket to mount the unit 20 in a casing (not shown). The casing and mounting method can be as shown in my prior application (patent) referred to above.

Figure 4:
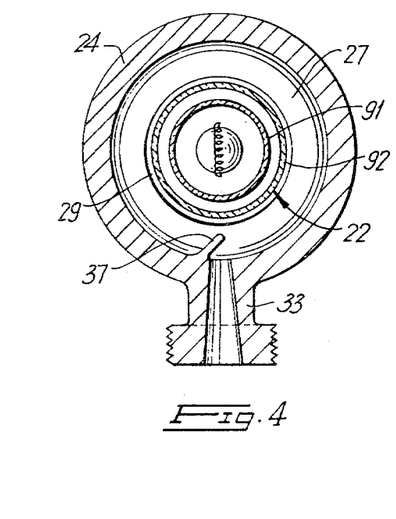
FIG. 4 is a sectional view on an enlarged scale taken along line IV—IV of FIG. 3 showing details of the tube and of a water inlet connection.

As can best be seen in FIG. 4, the end portion 24 has moulded therewith a fin 37 which deflects or imparts turbulence to the water flowing into the jacket via the connection 33.

Figure 4A:
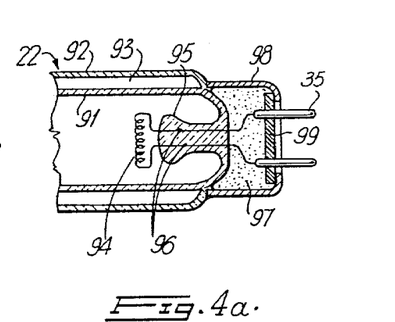
FIG. 4a is a fragmentary, longitudinal section of an end of the tube seen in FIGS. 3 and 4 illustrating details of the construction thereof.
Figure 5:
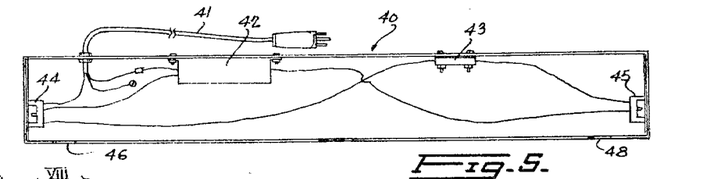
FIG. 5 is a plan view of a water sterilizer casing with the unit removed.

The internal structure of the double-walled tube 22 is shown in FIGS. 4 and 4a. This tube comprises an inner wall 91 and an outer wall 92 with a sealed cylindrical space 93 therebetween, which space preferably is evacuated. The electrode 94 is conventional and is conventionally mounted in a glass bead 95 projecting axially inward from the end of the inner tube wall 91. The electrode 94 is connected by leads 96 to the external terminals 35 which are supported in an insulating disc 99 mounted between a body 97 of epoxy resin and an inturned end rim on a metal tubular cap 98 secured to the end of the tube walls 91 and 92 where they meet and are fused together. The opposite end of the tube 22 is similar.

It will be apparent that the unit 20 as a whole has retained the feature of disposability while achieving the advantage of providing thermal insulation to the inner wall 91 of the tube 22 and hence to the radiation generating means, i.e. gas and electrodes within such inner wall. The temperature and hence efficiency of the tube 22 is thus retained. Moreover, in contrast to the old method described above of protecting the tube with a separate sheath, the use of a unitary double-wall construction enables the use of a vacuum in the space 93 between the walls. No dust or condensate can appear in this space and the thermal insulation is still further improved.

The entire unit can continue to be supported by a single mounting at each end (terminals 34, 35) as described below. The outer wall 92 is fused to the inner wall 91 at each end of the tube and thus there is no need for any further mounting means. This is in contrast to the separate sheath style of construction in which it was necessary to provide in the jacket separate mounting arrangements for the ends of the sheath and separate means for providing liquid tight seals between the ends of the sheath and the ends of the tube.

If preferred, an inert gas can be used instead of a vacuum in the space 93, or even dry air which of course, minimises the manufacturing costs. Whatever the medium in this space, it is positively sealed from the exterior of the tube by the permanently fused double-wall structure, and therefore the problems of dust and condensate are avoided. Clearly, from the viewpoint of thermal insulation, a vacuum is best.

It has been found experimentally that the additional reliability of performance of the present invention over my prior development under adverse conditions (water at or around 0° C.) has enabled a shorter tube to be used (as short as half the length of that formerly needed) while maintaining effective sterilization of the same throughput of water, i.e. the same rating.

Turning now to FIGS. 5 to 9, an elongated, rectangular shaped casing 40 is shown for encasing the disposable sterilizer unit 20. The casing has mounted thereon a standard electrical outlet 41, a standard ballast 42, a standard starter 43 and mounting receptacles 44 and 45 for the tube 22, together with their appropriate interconnected electrical wiring. The casing also includes three hemispherical notches 46, 47 and 48 in one side thereof.

Figure 6:
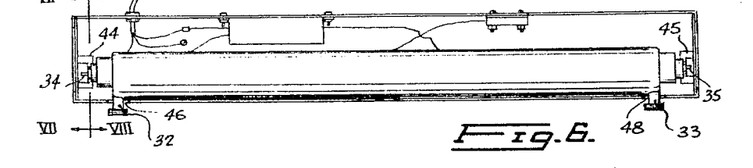
FIG. 6 is a similar view of the casing with the sterilizer unit installed.
Figure 7:
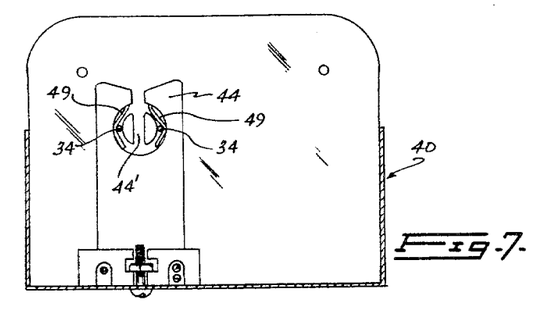
FIG. 7 is a view taken along line VII—VII of FIG. 6 showing details of the mounting receptacle in the casing.
Figure 8:
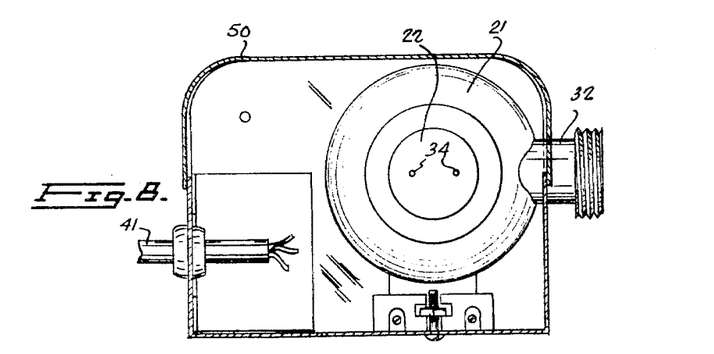
FIG. 8 is a view taken along line VIII—VIII of FIG. 6 showing more details.
Figures 9, 10:
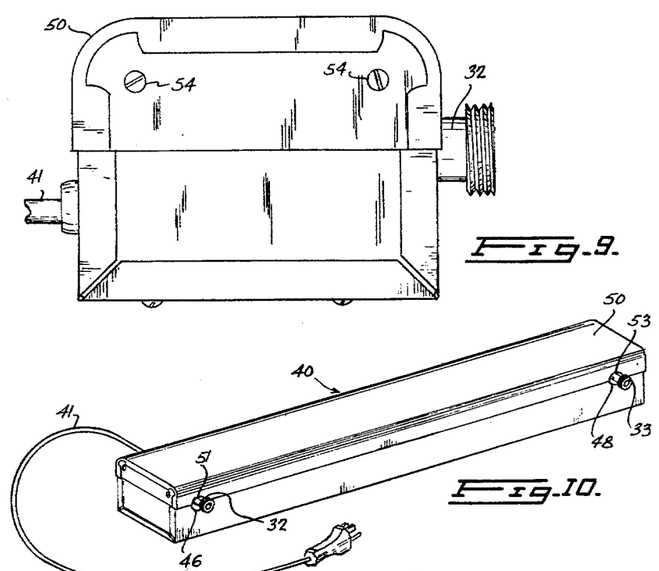
FIG. 9 is an end view of the casing with the cover mounted thereon.
FIG. 10 is a perspective view of a sterilizer assembly encasing a sterilizer unit.
Figure 11:
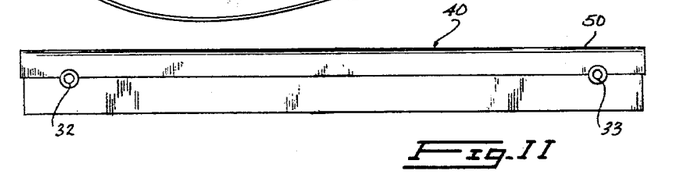
FIG. 11 is a front view of the sterilizer assembly.

As shown in FIG. 6, a sterilizer unit 20 of the kind shown in FIGS. 1 to 4 is placed in the casing 40 with the inlet connection 32 and outlet connection 33 facing up, so that the prongs 34 and 35 are in vertical alignment and fit into a slot 44' in the receptacles 44 and 45, respectively. The unit 20 is then rotated 90° to assume the position shown in FIGS. 6 and 7. The inlet connection 32 and outlet connection 33 fit into the slots 46 and 48, and the prongs are in horizontal alignment and in electrical contact with metallic springs 49, which are in turn connected to terminals located at the bottom of the receptacles 44 and 45. A cover 50 (see FIGS. 10 and 11), having hemispherical slots 51 and 53 complementary to the slots 46 to 48, is then fitted over the casing and fixed thereto by means of screws 54 at each end.

Figure 12:
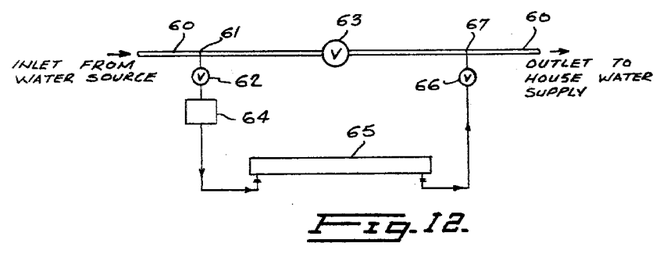
FIG. 12 is a schematic diagram of a water filtering system.

FIG. 12 shows in schematic form a water sterilizing system employing the invention. A water source inlet is connected to a water pipe 60, the water being diverted by means of a connection 61 and valves 62 and 63 through an activated carbon filter 64, and then through a sterilizer assembly 65 according to the invention. By means of a valve 66 and a connection 67 the sterilized water is passed back to the pipe 60 to an outlet leading to the house water supply. It is found to be desirable in practice to locate an activated carbon filter ahead of the sterilizer to remove particles from the water. However, the invention is still required following such filtering to kill bacteria, known to grow in activated carbon filters. The embodiments of FIGS. 13 and 14 provide for electrically sensing the flow of current through the tube.

Figure 13:
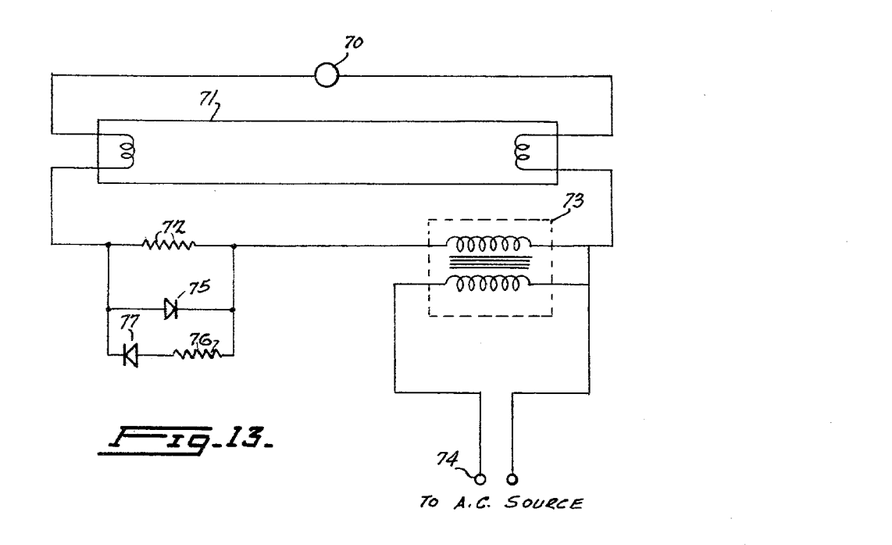
FIG. 13 shows a circuit arrangement for providing a visual means to detect failure of the tube.
Figure 14:
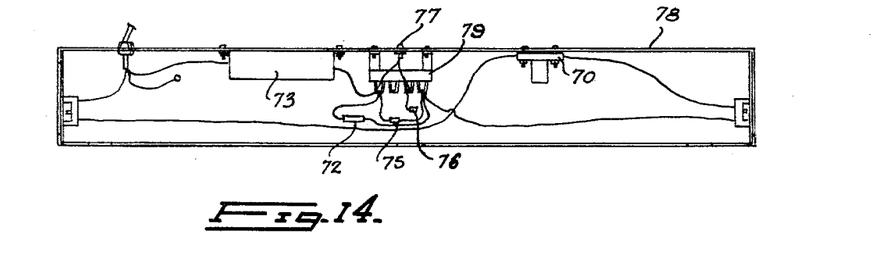
FIG. 14 is a plan view of a case (with cover removed) showing the mounting and connections of the circuit components of FIG. 13.

In FIG. 13, a conventional starter 70 for firing a tube is connected in a circuit with an ultra-violet tube 71, a resistor 72, a conventional ballast 73 and terminals 74 for connection to a conventional source of A.C. voltage. When current flows through the tube 71, a voltage drop is produced across the resistor, with a portion of the current flowing through a diode 75 during the negative half cycle of the A.C. voltage. This current flows through a current limiting resistor 76 and a light emitting diode (LED) 77. The parameters of the circuit are chosen so that as long as there is sufficient current flowing through the tube 71 to sterilize the water, the LED 77 remains on. When there is insufficient current or if the tube 71 is off, the LED also goes off, giving an indication that sterilization is not being achieved.

For a G30T8 tube, employing a FS4 starter and a L140FTPC ballast, it has been found that the following circuit components provide satisfactory results:

| | |
|---|---|
| resistor 72: | 10 W 6.8 ohms |
| diode 75: | IN4006 |
| resistor 76: | ½ W 27 ohms |
| LED 77: | OL30 |

Turning to FIG. 14, a casing 78 for housing the tube 71 is provided, including the starter 70, and the ballast 73. A terminal 79 is mounted on the casing for providing interconnections among the circuit components. The LED 77 is mounted to the wall of the casing and protrudes from the exterior thereof so that the light can be readily observed.

If the surfaces of the ultra-violet tube in contact with the water become coated with deposits, the effectiveness of the ultra-violet radiation can be seriously retarded. Thus, some sterilizers are provided with means to prevent the flow of water when insufficient light is being radiated by the tube.

One such arrangement is disclosed in Canadian Pat. No. 674,555 referred to above. The patent uses a photocell that is sensitive to ultra-violet light. The cell is connected in series with a current sensing relay, which in turn operates a valve that opens and closes the water inlet, depending on whether sufficient radiation is being received by the cell from the tube.

Figure 15:
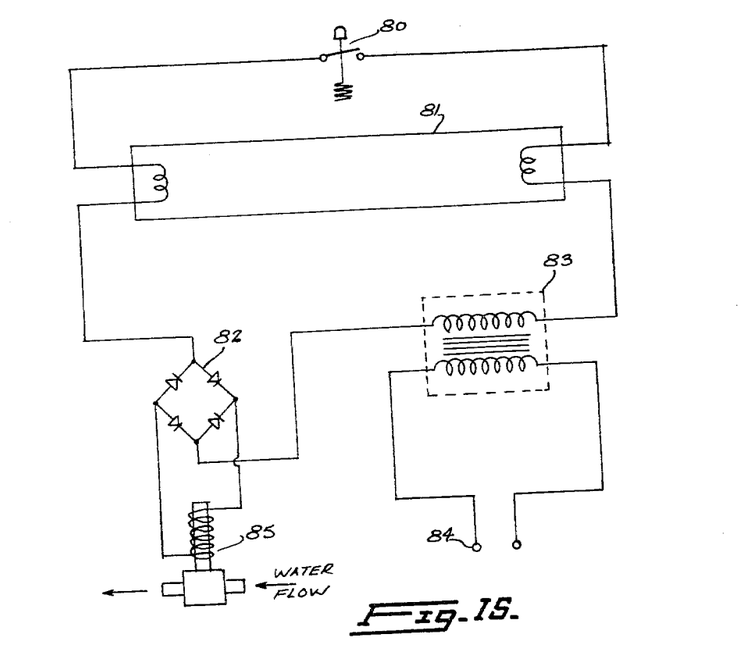
FIG. 15 shows a circuit arrangement for providing a stoppage of water flow upon failure of the tube.
Figure 16:
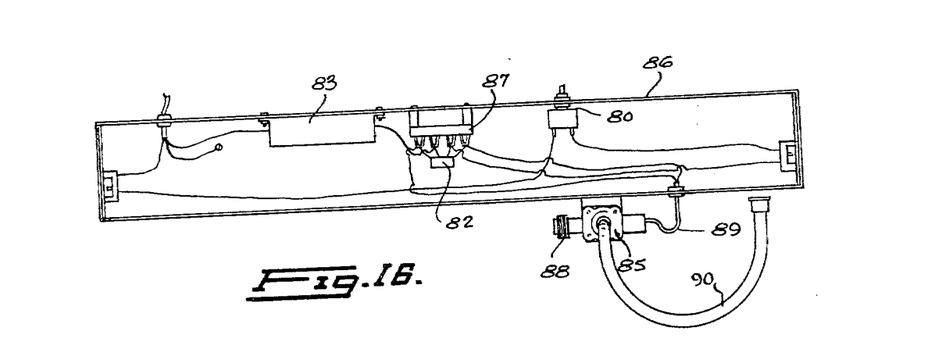
FIG. 16 is a plan view of a case (with cover removed) showing the mounting and connections of the circuit components of FIG. 15.

The embodiment of FIGS. 15 and 16 does not use a photocell or a relay, but instead directly senses the current flowing through the ultra-violet tube. A normally open spring return push button switch 80 for firing a tube is connected in circuit with an ultra-violet tube 81, a full wave rectifier 82, a conventional ballast 83 and terminals 84 for connection to a conventional source of A.C. voltage. The current flowing through the tube 81 is tapped off by the rectifier 82, with the rectified current flowing through the coil of a solenoid-operated, water control valve 85.

As long as sufficient D.C. current is flowing through the solenoid, the valve remains open, and the water continues to flow through the unit. However, if the current drops due to a failure or defect in the tube 81, the valve closes and the water flow is stopped. If the tube fails for any reason and the valve closes, the sterilizer cannot start again without operating the switch 80.

In FIG. 16, a casing 86 for housing the tube 81 is provided, including the starter 80 having its button protruding from the exterior of the casing and the ballast 83. A terminal 87 is mounted on the casing for providing interconnections and for mounting the rectifier 82. A water inlet 88 is connected to one side of the valve 85, which is mounted to the exterior of the casing 86. The output side of the valve 85 is connected by a short piece of hose 90 through an aperture in the casing (not shown) to the inlet connection of the disposable sterilizer unit. A conduit 89 houses the electrical leads that connect to the solenoid coil.

As will be apparent from the above discussion, sterilizer units fabricated in accordance with the teachings of the invention are within the budget of most home and cottage owners. Moreover, such sterilizer units can be installed without specialized skills, and can be economically thrown away when worn out or rendered relatively inefficient by residue build-up on the walls of jacket 21 and tube 22 and readily replaced with a new unit at low cost.

Thus, the invention satisfies a need for an inexpensive water sterilizer assembly that is of simple construction, easy to install without special skills, and which advantageously employs a disposable water sterilizer unit.

Applicant has also provided sterilizers with mechanisms for sensing the failure of the tube, either by producing a visual indication or by stopping the flow of water to the tube.

While the above provides a full and complete disclosure of the preferred embodiments of the invention, various modifications, alternate constructions and equivalents may be employed without departing from the true spirit and scope of the invention. Therefore the above description and illustrations should not be construed as limiting the scope of the invention which is defined by the appended claims.

I claim:

1. A disposable unit for sterilizing a liquid comprising:

an elongated jacket having an inner surface and opposing ends, an elongated tube including means for generating radiation to sterilize liquid in said jacket, said tube extending longitudinally along the interior of said jacket and having an outer surface, said inner and outer surfaces together defining a flow chamber for the liquid within said jacket around said tube, said tube being nonremovably received by said jacket, said jacket being substantially opaque to said radiation, means adjacent said opposing ends of said jacket for providing an inlet and an outlet for flow of liquid into said chamber and into direct contact with said outer surface of said tube for sterilization by the radiation therefrom and finally out of said outlet, and liquid tight seals at the ends of said jacket engaging respective ends of said tube to prevent outflow of liquid from the flow chamber except via said outlet, said tube ends each terminating in electrically conductive terminal means extending exteriorly of said jacket ends for applying electrical power to said tube and for providing mechanical support to said unit, said tube being a doublewalled tube having inner and outer cylindrical walls sealed together and spaced apart from each other, said outer surface of said tube being the outer surface of said outer wall and said means for generating radiation being located within said inner wall whereby the sealed space between said walls serves to provide thermal insulation between said generating means and the liquid in the flow chamber.

2. A unit according to claim 1, wherein said sealed space between the tube walls contains a dry gas.

3. A unit according to claim 1, wherein said sealed space between the tube walls is substantially evacuated.

4. The combination of a unit according to claim 1 and an elongated casing for mounting said unit, said casing having fixedly mounted therein spaced apart mounting means for receiving respective ones of said terminal means for thereby locating said unit in said casing, said mounting means including electric contact means for engaging said terminal means for connecting an external source of power to said terminal means to energize said tube.

5. The combination of claim 4 wherein said terminal means at each tube end comprises a pair of parallel prongs defining a first plane, and wherein each said mounting means in said casing includes socket means for receiving said prongs, said socket means comprising a first socket portion defining a second plane for enabling said prongs to enter said first portion by alignment of said first and second planes, said socket means further comprising arcuate socket portions extending around and communicating with said first socket portion to enable said prongs to enter said arcuate socket portions upon rotation of said unit in order to locate and retain said unit in said socket means, said electric contact means being located in said arcuate socket portions whereby upon said rotation said terminal means are connected to an external source of power.

* * * * *